United States Patent [19]

Boydman

[11] Patent Number: 5,069,668
[45] Date of Patent: Dec. 3, 1991

[54] PATIENT CONTROLLED ANALGESIA SYSTEM

[76] Inventor: Scott A. Boydman, 25447 Bryden Rd., Beachwood, Ohio 44122

[21] Appl. No.: 551,886

[22] Filed: Jul. 12, 1990

[51] Int. Cl.$^5$ ............................................. A61M 5/00
[52] U.S. Cl. ................................... 604/121; 604/131; 604/208
[58] Field of Search .................. 604/53, 121, 131, 208

[56] References Cited

U.S. PATENT DOCUMENTS

| | | | |
|---|---|---|---|
| 3,731,679 | 5/1973 | Wilhelmson et al. | 604/121 |
| 4,313,439 | 2/1982 | Babb et al. | 604/121 X |
| 4,627,839 | 12/1986 | Young | 604/121 |
| 4,828,551 | 5/1989 | Gertler | 604/208 |

OTHER PUBLICATIONS

Abbott Laboratories, North Chicago, Il. 60064, Brochure Entitled "PCA PLUS," Bearing Date 20-Oct. 88 and 1988 Copyright Date.
Gillies, G. W. A. & C. S. McArdle, "A Standard Microcomputer Linked to a Volume-Controlled Infusion Pump For Patient-Controlled Analgesia Research", Journal of Medical Engineering & Technology, V.10, No. 2, Mar./Apr. 1986, pp. 55-57.

*Primary Examiner*—William H. Grieb
*Attorney, Agent, or Firm*—David A. Burge

[57] ABSTRACT

A "dynamically" self-adjusting patient-responsive system for administering liquid medicine such as analgesia to patients as by infusion, with the "demand" of each patient for supplemental doses of drug being taken into account both in providing "on demand" "interval dosing" to supplement a "current rate" of background delivery of the drug to the patient, and in modifying the "current rate" of background delivery of the drug to more correctly correspond to the current needs of a particular patient. While "range" parameters (i.e., "limits" that define acceptable ranges of variance for various characteristics of a program of drug delivery that is intended to meet the very changeable current needs of a particular patient) are preset in accordance with the instructions of a physician, the hour-to-hour manner in which a drug is system-delivered to a particular patient principally is determined on a "dynamic" basis by the extent of the patient's current "demand" for supplemental drug infusion. By requiring that a "target" level of patient "demand" be maintained in order for a current "dynamically determined" level of drug delivery to be maintained (e.g., a certain number of button presses by the patient per pre-set time interval must be kept up, otherwise the infusion rate will be diminished automatically), infusions are automatically reduced as a patient becomes sedated, as healing progresses, or as patient demand lessens for these and/or other reasons, whereby safety is enhanced and infusion is conformed to a minimum that is consistent with current needs of a patient, within physician-prescribed limits.

25 Claims, 2 Drawing Sheets

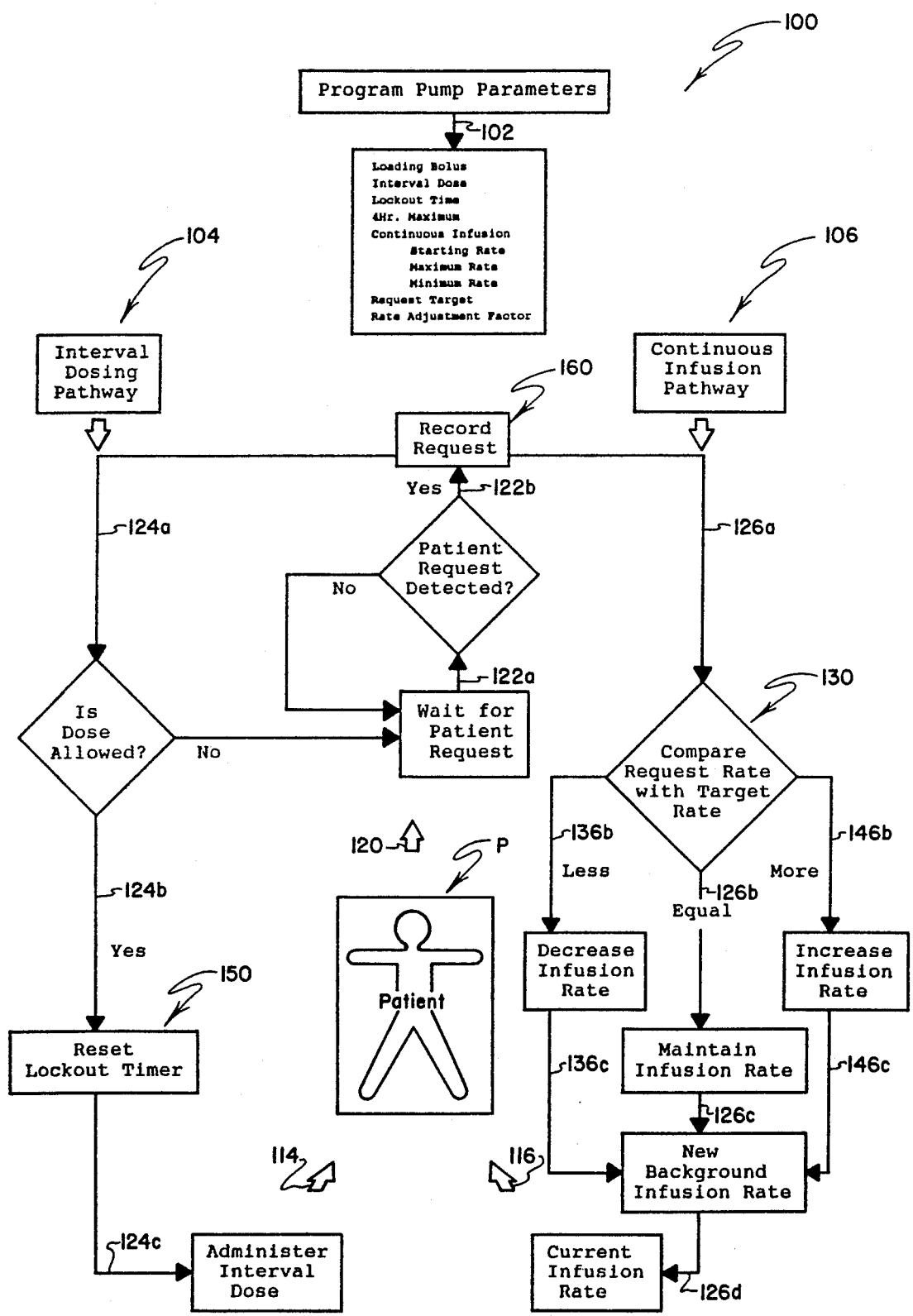

PATIENT CONTROLLED ANALGESIA SYSTEM

BACKGROUND OF THE INVENTION

1. Field of the Invention

The present invention relates to the automated administration of liquid medicine to patients, and is particularly well suited to provide a patient controlled analgesia (PCA) system for administering analgesia as by intravenous infusion. More particularly, the present invention relates to a "dynamically" self-adjusting patient-responsive system that serves both to maintain infusion delivery of a drug within physician-prescribed limits for a particular patient, and to utilize patient input in a plurality of ways to provide "on demand" "interval dosing" to supplement a "current rate" of background delivery of the drug to the patient, so that the resulting infusion delivery of drug is conformed to a minimum that is consistent with the patient's current needs, within physician-prescribed limits.

2. Prior Art

The automated dispensing of liquid medicine, such as analgesia, as by infusion to relieve postoperative pain, to relieve pain caused by disease such as cancer, and/or to relieve other severe pain is increasingly being effected by utilizing "presettable" (i.e., "programmable") infusion pump units. Typically, an infusion pump unit is provided with a quantity of liquid analgesia, and buttons (or other suitable controls) of the pump unit are operated to "preset" or "program" the pump unit to dispense analgesia in accordance with a plan of physician-prescribed dosages. Because the drug to be dispensed often is of narcotic origin, typically morphine, care must be taken in "instructing" the pump unit as by correctly entering the prescribed series of commands that are to be carried out by the unit in order to suitably meet the needs of a particular patient.

To prevent the entry of unsuitable commands and/or the entry of commands by unauthorized persons, infusion pump units typically are provided with security features including keylock-controlled switches and requirements for entry of authorization codes (e.g., "passwords") before an infusion pump unit will recognize and carry out newly received commands.

Programmable infusion pumps have gained a reputation for performing reliably to timely dispense prescribed doses of drugs such as analgesia. In view of the reliability that has been demonstrated by infusion pump units, and inasmuch as the use of infusion pump units often helps to free trained nurses for functions other than the hour-to-hour routine administration of medication, increasingly widespread use is being made of infusion pump units in hospitals and in long term care facilities. In view of the demand that exists for these units, the units now are commercially available from a variety of medical supply houses.

In one widely marketed form, programmable infusion pumps are designed simply to provide a reliable supply of pain medication in accordance with a fixed dosage prescription provided by a physician. Pumps that are capable of providing fixed-dose modes of delivery of analgesia are described in U.S. Pat. Nos. 4,627,839 and 4,828,551 issued Dec. 9, 1986 and May 9, 1989, respectively, the disclosures of which are incorporated herein by reference.

In an updated form, and as is discussed in U.S. Pat. No. 4,627,839, some programmable infusion pumps are capable of functioning to deliver analgesia in either of two ways, namely in a fixed-dose mode of delivery, or in what is called a "patient controlled analgesia" (PCA) mode, namely a delivery mode wherein the unit is responsive to patient "input" or "demand" for analgesia, with the response of such units being constrained by physician-prescribed limits that are designed to avoid such problems as "overdose." The invention that forms the subject matter of U.S. Pat. No. 4,627,839 is intended to provide a means to "convert" existing programmable infusion pumps from a form that is capable only of operating in a fixed-dose mode of delivery to a form that will enable such pumps to operate either in a fixed-dose mode or in a PCA mode.

In still another form, Abbott Laboratories of North Chicago, Ill. 60064 has begun marketing a programmable infusion pump unit under the designation "PCA Plus, Model 4100." The Abbott unit features a capability to operate 1) in a fixed-dose delivery mode, 2) in a PCA delivery mode, or 3) in something of a combination of "fixed-dose" and "PCA" modes. In the "combined" mode, the Abbott unit can be preset to deliver analgesia simultaneously A) in a "fixed-dose" mode (wherein the resulting rate at which analgesia is delivered to the patient can be referred to as a "current rate'-"—i.e., a rate that is "preset" and therefore is "fixed" as opposed to being variable in response to patient demand and need), and B) in "PCA mode" response to patient demand (with the "PCA mode" providing what can be referred to as a series of "interval doses" that supplement the "current rate" delivery of analgesia).

The Abbott unit is provided with means for keeping track of the supply of analgesia that is delivered to a patient. The Abbott unit also has a number of other features including safety features that are of a type that is well known to those who are skilled in the art, with examples being 1) means for monitoring the quantity of analgesia that has been administered to the patient to prevent overdose and/or undesirable side effects that may result from doses that are excessive, and 2) means for monitoring and controlling the time interval that must transpire between consecutive administrations of "interval doses."

Not addressed by the proposal of the Abbott unit or by other prior proposals is a very important need that arises during "combined mode" delivery of analgesia to a patient (i.e., a mode that includes the dispensing of analgesia both 1) by establishing a "current rate" for delivery of a "background" dosage of analgesia, and 2) by permitting the background delivery to be supplemented by "on demand" doses that are requested by "demand" input from the patient)—namely the very real need for not only the "PCA mode" of analgesia delivery to be responsive to patient demand, but also for the "current rate mode" of analgesia delivery to likewise be responsive to patient demand.

Neither the Abbott proposal nor other prior proposals provide for a "dynamically" adjusted "resulting rate" of infusion delivery of drug to a patient—wherein the resulting infusion rate is diminished automatically in response to failure of a patient to maintain a preset "target" level of demand (e.g., a certain number of button presses per pre-set time interval). Thus, these units do not function to automatically reduce infusion rate as a patient becomes sedated, or as healing progresses, or as patient demand diminishes as the result of these or other reasons. Nor do these units function to conform the resulting infusion rate to a minimum that is consistent with current needs of a patient, within physician-prescribed limits.

In the study of analgesic medicine, it is well accepted and understood that there are no "common denominators" that will enable a physician to accurately predict the analgesia needs of particular patients, nor even to predict with accuracy how the analgesia needs of particular patients will vary depending on a host of factors that interact, such as the time of day, the level of activity of the patient, whether the patient is standing, sitting or reclining, etc. Differences in ranges of required analgesia can be dramatic even among physically similar patients who are subjected to very similar pain-producing circumstances. Thus, while systems that embody prior proposals for automated dispensing systems for analgesia are to some extent "patient controlled," the fact remains that, in a number of important ways in which these systems can be preset to effect delivery of medication, these systems are not responsive to patient need to a desired degree.

Systems that embody prior proposals do not make the fullest possible use of patient "demand" information to modify the "resulting rate" at which medication is infusion delivered to patients. Such systems are seriously and severely limited by the fact that the type of infusion delivery they provide is defined by a static set of predefined parameters—by settings that do not vary within physician-prescribed ranges based upon patient input—i.e., by settings that may be very inappropriate for a particular patient inasmuch as they were prescribed by a physician who typically is not in frequent contact with the patient, and who can only guess at the range of values that are most appropriate for use with any particular patient under the particular circumstances that are at hand.

Stated in another way, the systems of prior proposals are not nearly as "patient responsive" as they need to be in order to accommodate the very significant differences in analgesia dosage levels that are appropriate for use with different patients, or that are needed by a particular patient at different times of the day or as the patient's schedule of activities moves among states of sleep, alert restfulness, and various stages of physical exertion. Most particularly, the systems of prior proposals do not provide "dynamically" self-adjusting patient-responsive systems that serve both to maintain infusion delivery of a drug within physician-prescribed limits for a particular patient, and to utilize patient input in a plurality of ways to provide "on demand" "interval dosing" to supplement a "current rate" of background delivery of the drug to the patient, so that the resulting infusion delivery of drug is conformed to a minimum that is consistent with the patient's current needs, within physician-prescribed limits.

As regards the level of analgesia that is needed by a particular patient at a particular time, it often has been observed that the "best" pain expert for a particular patient is the patient himself or herself—as opposed to the patient's physician. While physicians may have the knowledge and experience that is needed to determine a suitable analgesia dosage range that ought to be "tried" in an effort to meet the needs of a particular patient, it tends to be the patient, not the physician, who is the best judge of the dosage within the physician-set range that best serves the needs of the patient at a particular time and under the circumstances of the moment. Thus, automated analgesia dispensing equipment that is set in accordance with input received solely from the physician has an inherent drawback.

Moreover, it has been observed that the effectiveness of the administration of analgesia often can be enhanced when the dispensing of the drug is being controlled to the fullest possible degree by the patient—with safety considerations being kept in mind to prevent overdose In some instances it has been observed that, with patient control, the quantity of a pain-relieving drug that is needed to provide a desired degree of relief is diminished, patient comfort is enhanced, and/or the severity of side effects from taking the drug is lessened. Accordingly, automated dispensing machines that make minimal use of patient input and rely primarily on physician input may, in some instances, malserve the best interests of the patient.

SUMMARY OF THE INVENTION

The present invention addresses the foregoing and other needs by providing a "dynamic" patient responsive system for administering liquid medicine such as analgesia to patients as by infusion, with the "demand" of each patient for supplemental doses of drug being taken into account both in providing "on demand" "interval dosing" to supplement a "current rate" of background delivery of the drug to the patient, and in modifying the "current rate" of background delivery of the drug to more correctly correspond to the current needs of a particular patient. While "range" parameters (i.e., "limits" that define acceptable ranges of variance for various characteristics of a program of drug delivery that is intended to meet the very changeable current needs of a particular patient) are preset in accordance with the instructions of a physician, the hour-to-hour manner in which a drug such as analgesia is system-delivered to a particular patient principally is determined on a "dynamic" basis by the extent of the patient's current "demand" for supplemental drug infusion.

By requiring that a "target" level of patient "demand" be maintained in order for a current "dynamically determined" level of drug delivery to be maintained (e.g., a certain number of button presses by the patient per preset time interval must be kept up, otherwise the infusion rate of "background" delivery of drug will be diminished automatically), infusions are automatically reduced as a patient becomes sedated, as healing progresses, or as patient demand lessens for these and/or other reasons—whereby safety is enhanced and infusion is conformed to a minimum that is consistent with current needs of a patient, within physician-prescribed limits. Likewise, during times when the level of current delivery of drug fails to provide the patient with sufficient analgesia, an increased number of button presses by the patient will result in a "dynamic" increase in the rate of "background" delivery of drug to the patient—whereby a more optimal level of drug delivery automatically is effected without the need for a physician or nurse to intercede as by changing the instructions that are governing the operation of the system.

Typically, a "demand" made by a patient for a supplemental dose of analgesia is implemented promptly (as by infusing an "interval dose" of analgesia to supplement the "current rate" at which analgesia is being delivered on a regular or "background" basis to the patient—so long as the delivery of the supplemental dose will not cause the delivery of drug to exceed preset "range" parameters); and, "demand" data is utilized to modify the "current rate" at which analgesia is delivered on a regular or "background" basis to the patient. Thus, the delivery of a drug such as analgesia to a patient is entirely "dynamically" controlled as a function of patient "demand" to give the patient as much control over drug delivery as can safely be provided, while minimizing the quantity of drug that is delivered to conform as closely as possible to the precise needs of the patient.

In the preferred practice of the present invention, patient input preferably is utilized in at least two ways to modify the way in which the analgesia delivery system serves a patient. In a first way, a "demand" made by a patient for analgesia is implemented promptly as by delivering an "interval dose" of analgesia to supplement the "current rate" at which analgesia is being delivered on a regular basis to the patient; however, an "interval dose" is provided only 1) if the requested demand can be executed without violating a preset "lockout interval" of time that must transpire between sequentially dispenses "interval doses" of analgesia, and 2) if the demanded "interval dose" will not cause the cumulative quantity of analgesia that has been dispensed to exceed a predetermined upper limit for analgesia that has been dispensed within a given period of time. In a second way, "demand" data is utilized to modify the "current rate" at which analgesia is delivered on a regular basis to the patient.

In the most preferred practice of the present invention, a "target" rate of patient "demand" is pre-set—a level of "demand" per pre-set interval of time that must be maintained by the patient as by providing a certain minimum level of button presses per pre-set time interval (e.g., per half hour, or per hour, etc.) in order for the current level of infusion delivery of drug to be maintained without being automatically diminished. By this arrangement, infusions are automatically reduced as a patient becomes sedated, as healing progresses so that a lesser quantity of analgesia is needed, or as patient demand diminishes for these and/or other reasons—whereby safety is enhanced, and infusion is conformed to a minimum that is consistent with current needs of a patient, within physician-prescribed limits.

In one form of practice, the present invention relates to a highly advantageous method of administering analgesia on a "patient controlled" basis. The system provides a combination of delivery systems for analgesia, both of which are patient responsive. Analgesia is delivered to the patient 1) on a regular basis at a "current rate," and 2) "on demand" in "interval doses," with the "interval doses" being supplied quickly in response to patient demand (assuming that what is being requested does not exceed preset safety limits), and more decidedly as by accumulating and responding to "demand" data so as to alter the "current rate" at which analgesia is being delivered to the patient, whereby the patient's needs are met far better by the system of the present invention than by the systems of prior proposals.

In accordance with the most preferred form of practice of the present invention, an initial setup is made to instruct an infusion apparatus to deliver analgesia in accordance with a three-part plan that is prescribed by a physician. The first part of the plan for delivering analgesia to a patient has to do with the setting of a "current rate" at which analgesia will be delivered to the patient under conditions of "patient demand" for analgesia being equal to a "target demand" that has been pre-set by the physician. The second part of the delivery plan has to do with setting the parameters that will control the supply of "interval doses" of analgesia to a patient to supplement the "current rate" of infusion if "patient demand" for analgesia exceeds the "target demand." The third part of the delivery plan has to do with prescribing how data that has been collected and recorded (data that characterizes the need of a particular patient for analgesia) is to be used in a plurality of ways to periodically modify the combined resulting rate at which analgesia is delivered to the patient as by reducing it "automatically" the patient becomes sedated, as healing progresses so that a lesser quantity of analgesia is needed, or as "patient demand" diminishes for these and/or other reasons—whereby safety is enhanced, and infusion is conformed to a minimum that is consistent with current needs of a patient, within physician-prescribed limits.

BRIEF DESCRIPTION OF THE DRAWINGS

These and other features, and a fuller understanding of the invention may be had by referring to the description and claims that follow, taken in conjunction with the accompanying drawings, wherein:

DESCRIPTION OF THE PREFERRED EMBODIMENT

Figure 1:
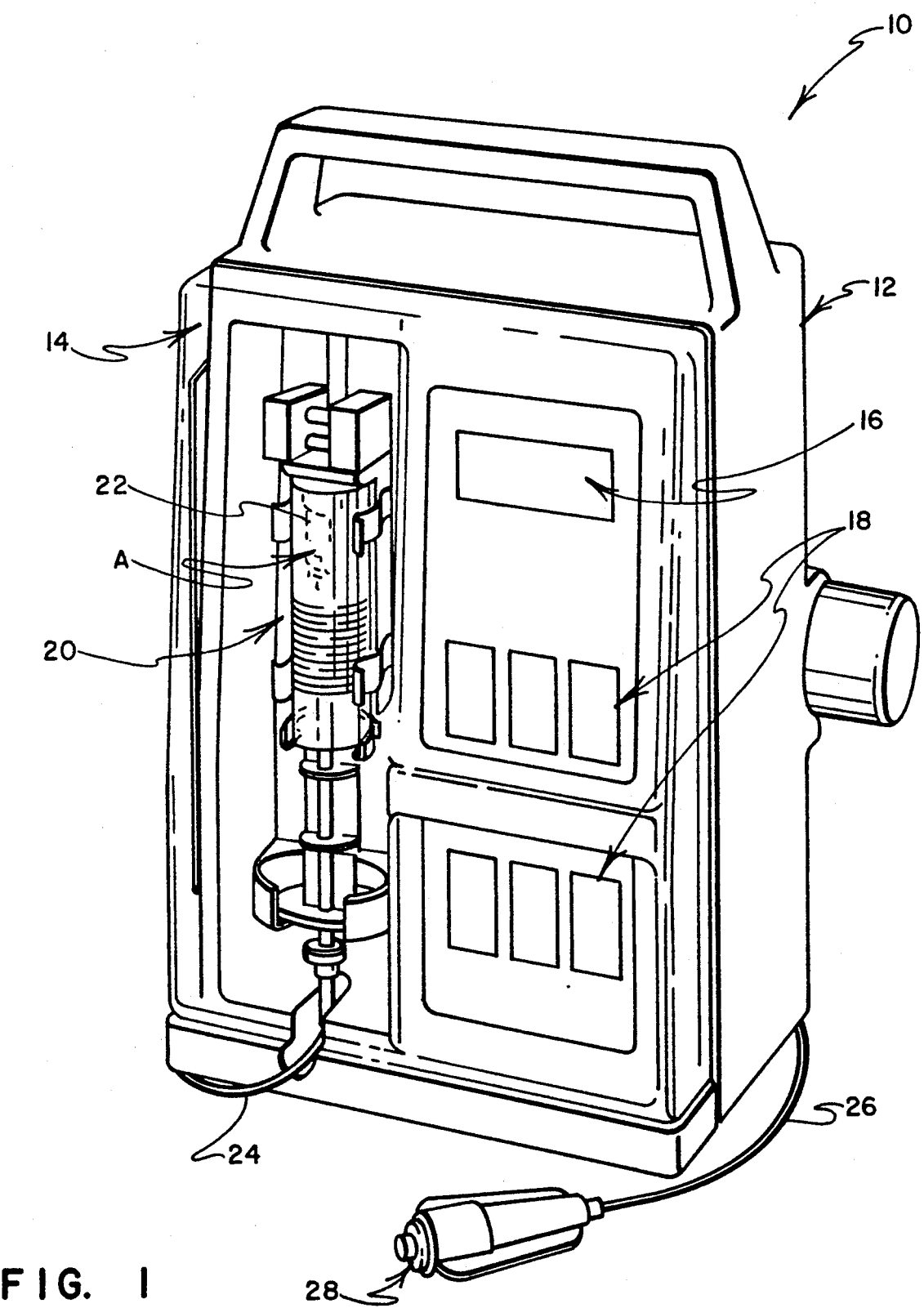
FIG. 1 is a perspective view of an infusion pump unit of the general type that can be utilized to carry out the preferred practice of the present invention; and, FIG. 2 is a flow chart schematically illustrating a preferred method of practice of the present invention that is intended for use with an infusion pump unit of the general type that is depicted in FIG. 1.

Inasmuch as the system of the present invention is not hardware-restricted in nature but rather provides a method for delivering liquid medicine for infusion into a patient—a method that can be carried out as by utilizing a wide variety of combinations and arrangements of hardware of a type and kind that are readily understood by those who are skilled in the art—it is neither necessary nor appropriate for the present description to go into significant detail regarding the construction and arrangement of hardware components that can be utilized to carry out the preferred practice of the present invention.

What is preferred in the way of apparatus for carrying out the best mode known to the inventor for practicing the method of the present invention is an infusion pump unit that has presettable controls that will enable commands that are representative of the parameters that define the method of the invention to be entered into and carried out by the pump unit. Infusion pumps that are provided with various forms of presettable controls are described in detail in U.S. Pat. Nos. 4,627,839 and 4,828,551, the disclosures of which are incorporated herein by reference. Other forms of such apparatus are commercially available and are known to those who are skilled in the art.

The Prior Art Apparatus Depicted in FIG. 1

With the foregoing as background, it will be understood 1) that the commercially available infusion pump that is depicted in FIG. 1 is not a part of the present invention, 2) that the unit that is depicted in FIG. 1 is included in the drawings hereof simply to assure that the reader does not misunderstand the general nature of the unit that is envisioned as representing the most preferred means for carrying out the practice of the present invention, and 3) that other kinds and types of units (i.e., other combinations and arrangements of hardware) also can be utilized in practicing the method of the present invention while preserving the spirit and scope thereof.

Referring to FIG. 1, a microprocessor controlled infusion pump unit of the general type that can be employed to carry out the preferred practice of the present invention is indicated generally by the numeral 10. The unit 10 includes a housing that is generally indicated by the numeral 12. The housing 12 has a front face that is generally indicated by the numeral 14. A display screen 16 and a series of controls 18 are provided on the front face 14 for purposes of presetting operating parameters of the pump unit 10.

A pumping mechanism (portions of which are indicated generally by the numeral 20) form a part of the pump unit 10. The pumping mechanism 20 functions to dispense liquid medicine such as analgesia (indicated generally by the letter "A") from a reservoir 22 into a tube 24 that is connectable to a conventional catheter (not shown) for delivery by intravenous infusion to a patient.

A flexible electrical cable 26 forms a part of the unit 10 and projects from the housing 12 to provide a remote push button control 28 that can be operated by a patient so as to enter a "demand" for analgesia.

The unit 10 does not form a part of the present invention, and is depicted and described herein only for purposes of illustrating the general appearance of (and a typical arrangements of components of) the type of infusion pump apparatus that preferably is utilized in carrying out the best mode of practicing the invention that presently is known to the inventor named herein. What the unit 10 provides is a pump unit "assemblage" of components having desirable features that have been developed through the course of many years, and that combine to provide a pump unit 10 that is capable of receiving a wide variety of commands (as by pushing buttons or other controls 18 in conjunction with viewing a changing display of information that is presented on the screen 16), and of carrying out the entered commands as by causing the pumping mechanism 20 to dispense into the tube 24 a series of carefully timed, precisely determined quantities of liquid medicine from the reservoir or cannula 22 for delivery by the tube 24 through a conventional catheter (not shown) into a patient's blood vein. Typically the entering of commands into the unit 10 must be accompanied by the entering of an access code that is known only to authorized personnel (a "password" or the like), and by operating one or more key lock controlled mechanisms (not shown) that operate electrical switches and/or safety enclosure doors that limit access to and operation of the controls 18. One proposed arrangement of components of this general type is described in Pat. No. 4,627,839, the disclosure of which is incorporated herein by reference.

In view of the foregoing discussion, it will be understood that "pre-settable" or "programmable" apparatus for infusing patients intravenously with a series or sequence of very exacting doses spaced apart by exact, preset time intervals, and/or units that respond to patient "demand," are well known to those skilled in the art. The technology for providing pump units that will receive desired types of commands, that will accept predetermined ranges for variables, that will comply with desired limits that control how the units will function, exists and already is embodied in commercially available apparatus, such as the pump unit 10. Modifying or enhancing such apparatus to accept new commands, ranges for an added variety of variables, permitted limits to govern the operation of such units, and other such information is well within the capability and understanding of those who are skilled in the art—as is providing such units with a capability to store entered data, to compare stored data with pre-set values, and to respond to data comparisons as by generating and executing certain commands that are in accordance with instructions that are provided to such units.

Because the present invention relates principally to a method of operating a "pre-settable" or "programmable" infusion pump, it does not matter whether the instructions that are to be imparted to the pump unit are inputted as by the setting of dials, the flipping of switches, the pushing of buttons, or by more sophisticated techniques such as providing at least a portion of the instructions in encoded format on microprocessor chips or the like. In preferred practice, the use of a presettable microprocessor controlled infusion pump unit of the type that is designated by the numeral 10 in FIG. 1 represents the best mode presently known to the inventor for carrying out the practice of the method of the present invention.

The Method of the Present Invention

Referring to FIG. 2, the method of the present invention for delivering analgesia in accordance with preset parameters and taking into account patient "demand" as registered by operating a control such as the push button 28 (shown in FIG. 1) is depicted by a schematic system diagram, with the depicted system being designated generally by the numeral 100.

Initial input is provided to the system 100 as is indicated by an arrow 102. What the arrow 102 depicts is a "presetting" or "programming" of system controls as by setting dials, flipping switches, pushing buttons, or by more sophisticated techniques such as providing at least a portion of the instructions in encoded format on microprocessor chips or the like (none of which are depicted inasmuch as the character of the structure used to carry out the method of the invention is not critical, and inasmuch as commercially available infusion pump units of the general type that can be used to carry out the practice of the present invention are well known to those who are skilled in the art).

A number of parameters are input to the system 100, as is indicated by the arrow 102 in FIG. 2, with the following providing a typical set of these input parameters:

| Setting of Initial "Current Rate" for "Background" Infusion | |
|---|---|
| Loading (bolus) dose of analgesia—in this example, morphine | 3 mg |
| Starting infusion rate | 2 mg/hr |
| Setting of Parameters That Control "Interval Dose" Delivery | |
| Interval dose | 1 mg |
| Lockout interval | 10 minutes |
| Setting of Parameters That Cause Changes in "Background" Infusion | |
| Target number of requests | 2 per hr |
| Rate adjustment factor | +/−1 mg/hr |
| Setting of Limits That Define Outside Limits of Infusion Dosage | |

-continued

| | |
|---|---|
| Infusion rate maximum | 5 mg/hr |
| Infusion rate minimum | 0.1 mg/hr |
| Four hour maximum | 28 mg |

The system 100 begins its operation by receiving and recording physician-prescribed input, as is indicated by the numeral 102. The physician-prescribed input 102 will be utilized (as is explained in a continuation of a discussion of the example) to control, govern and flexibly limit the operation of an infusion pump unit (such as the previously described pump 10) to deliver liquid medicine such as analgesia to a patient "P" (as is shown toward the lower central part of the diagram of FIG. 2).

Before returning to the example, a brief description will be provided so that what is depicted in FIG. 2 will be readily understood. The left side of FIG. 2, as indicated generally by the numeral 104, has to do with the supplying of medicine to the patient "P" as by "interval dosing" —i.e., the supplying of medicine to the patient "P" in response to "patient demand" which is indicated generally by the arrow 114. The right side of FIG. 2, as indicated generally by the numeral 106, has to do with the supplying of medicine to the patient "P" as by "continuous infusion" dosing, which is indicated generally by the arrow 116. Patient "demand" (typically provided by the patient's pressing a button such as the button 28 shown in FIG. 1 as forming a part of the unit 10) is indicated by an arrow 120.

Returning to the example (but referring also to FIG. 2 from time to time as the example is related), the input 102 described above is entered into the system 100 to govern its operation. A post-operative patient "P" is started on an infusion pump unit (such as the unit 10 shown in FIG. 1) that has been "instructed" so as to embody the system 100. Typically, the patient is "hooked up" to such a unit in the recovery room of a hospital.

The dispensing of analgesia by the system 100 is begun, as guided by the preset parameters that are listed above (i.e., the "input" 102). How these parameters influence and control the infusion of analgesia will now be explained.

The "loading" or "bolus" dose of analgesia, namely 3 mg of morphine, is delivered to the patient at the start of system operation. In FIG. 2, this is indicated by arrows that are a part of the "interval" dosing function 104 of the system 100, namely arrows 124a, 124b, 124c and 114. Depending on the a number of factors that have to do with the condition of the patient as well as what other drugs already have been given to the patient, a higher or lower "bolus" dose may be preset by the physician, or no "bolus" dose at all may be used.

The "starting infusion rate" (i.e., the "current rate" at which the system is set to begin infusing analgesia to the patient) is 2 mg/hr. In FIG. 2, this is indicated by arrows that are a part of the "continuous infusion" portion 106 of the system 100, namely arrows 126a, 126b, 126c, 126d and 116. Thus, during the first hour after the patient is hooked up to the system, he or she receives 2 mg of morphine.

The physician has preset a "target number of requests" for patient "demand" as being 2 per hour—which information comprises a part of the input 102. As the patient "P" recovers from anesthetic and regains consciousness, an explanation is given to the patient of the purpose for his or her being connected to the infusion system 100; the location of a "demand input control" (such as the push button 28 shown in FIG. 1) is pointed out to the patient so that he or she can provide "demand" input 120 to the system 100 as by operating the control; and an explanation is given to the patient as to the "expectation" that the physician has preset into the system 100, namely that the patient will want to continue the "current rate" of infusion of analgesia on an "as is" basis by inputting two demands 120 per hour to the system 100.

The "rate adjustment factor" has been set at plus or minus 1 mg/hr. If the number of demands that are inputted to the system 100 during any one designated time period (in this example, all rates have been set in a very simple way, as by specifying "one hour" as the time interval over which they are measured) is more or less than the preset target number "2", then, during the next hour, the "current rate" of background infusion will be adjusted correspondingly upwardly or downwardly by 1 mg/hr.—except that, if changing the "current rate" in this way would cause one of the preset limits to be violated, the change will not be made. Thus, if the change would cause the infusion rate to exceed 5 mg/hr or to drop below 0.1 mg/hr, any change that is made will be modified so that it does not exceed these limits. Likewise, the preset limit of 28 mg/4 hr will not be permitted to be exceeded. The provision of a lower limit of 0.1 mg/hr is desirable so that flow is continued through the catheter (not shown) that is utilized to connect the system 100 to the patient "P"—with this minimal flow serving to keep the needle clean and open so that it will function properly.

Referring to FIG. 2, when a patient "demand" 120 is detected, it is passed along a pathway that is indicated by the arrows 122a, 122b, and thence both 1) leftwardly (as is indicated by the arrow 124a) into the interval dosing control portion 104 of the system 100, and 2) rightwardly (as is indicated by the arrow 126a) into the continuous infusion control portion 106 of the system 100.

On the continuous infusion side of the system 106, a patient demand 120 is compared, by a continuous infusion controller 130, to determine whether, during a given time interval (in this example, one hour is utilized), a total number of demands 120 has been received that is less than, equal to, or greater than the pre-set target rate of 2 per hour. If the patient demand 120 brings the total demands per prescribed time interval to the target number 2 (without exceeding this number), the routing of a pump signal that causes the continuous infusion rate to continue at the same level as it has been running (namely the starting infusion rate of 2 mg/hr) is indicated by the arrows 126b, 126c, 126d and 116. If the number of patient demands 120 received at the end of each hour by the controller 130 totals less than the target value of 2, then the routing of a pump adjustment signal that causes the continuous infusion rate to be adjusted downwardly by the amount of the rate adjustment factor, namely 1 mg/hr, is indicated by arrows 136b, 136c, 126d and 116. If the number of patient demands 120 received at the end of each hour by the controller 130 totals more than the target value of 2, then the routing of a pump adjustment signal that causes the continuous infusion rate to be adjusted upwardly by the amount of the rate adjustment factor, namely 1 mg/hr, is indicated by arrows 146b, 146c, 126d and 116.

As regards interval dosing, whether a particular patient demand 120 is operable to cause delivery of an interval dose 114 to the patient "P" depends on whether a "lockout timer" 150 permits a pump signal to pass from arrow 124b to 124c. Because a "lockout interval" of 10 minutes has been preset by the physician to prescribe a period of time that must pass before a demand for an "interval dose" 114 can be administered to the patient "P" by the system 100, any demands made for "interval doses" that are not spaced by at least 10 minutes from the time at which the most recent "interval dose" 114 was infused will not be honored.

In the way described above (and depicted in the diagram of FIG. 2), the system 100 serves to control the administering of "interval doses" 114 of analgesia to the patient "P" to supplement, as needed, the "current rate" 116 background dosage of analgesia that also is being administered to the patient "P". However, the system 100 also operates in another way to modify the "current rate" of background infusion in response to patient demand for analgesia—but with the pre-set operating limits 102 still being honored by the system 100 so as to assure that the infusion of analgesia to the patient takes place within physician preset ranges of permissible limits.

Modification of the "current rate" of background infusion takes place in the following way. The actual number of patient "demands" 120 are recorded, as is indicated by the numeral 160 in FIG. 2, with this recording taking place independently of whether the demands 120 have been honored by the "interval dosing" portion 104 of the system 100 (i.e., if the patient requests supplemental dosing more frequently than the "lockout interval" timer 150 will permit, some of the patient's demands 120 will not be honored—but, nonetheless, they will be counted by the recorder 160). The infusion control 130 then compares the actual recorded response rate with the target rate for patient "demands" 120, and, if the actual response rate differs from the target rate, adjustment signals (indicated by arrows 136b, 136c or 146b, 146c) are generated to cause the continuous infusion rate to be lowered or raised by the pre-set value of the rate adjustment factor, with progressive adjustments typically being made at the end of each preset interval of time (such as one hour, in the example presented here).

The selection of the interval of time for the making of adjustments in continuous infusion rate can be different from or equal to the "lockout interval" of time that is utilized by the "interval dosing" side of the system 100. Moreover, the interval of time used for adjusting the continuous infusion rate so as to "increase" the continuous infusion rate can differ from the interval of time used to diminish the continuous infusion rate—the thought being that, if the patient "P" is providing many demands "P" within a brief interval of time, there is probably justification for stepping up the continuous infusion rate relatively rapidly, within physician-preset limits; whereas, if the patient "P" has simply fallen asleep briefly and has therefore failed to provide any demands 120 to the system 100, perhaps the continuous infusion rate should not be dropped down rapidly, for the patient may shortly wake up and, if his supply of analgesia has been cut back drastically, he will likely input many demands 120 to the system 100 due to his experiencing an increase in severe pain.

It often is important to provide a way to assure that the system 100 will not behave in a way that causes the continuous infusion rate to be cut back too rapidly. To achieve this result, the controller 130 can be told to behave in special, predetermined ways in deciding whether to cut back on the continuous infusion flow rate. For example, if the rate at which demands 120 are being received by the system 100 is less than the preset target rate, a function that could be executed by the controller 130 is to lengthen the interval of time during which demands 120 are counted. The controller 130 could lengthen the interval to twice its normal length, and, if the total umber of demands received within the lengthened period of time is found to equal the target rate, the continuous infusion rate could be maintained without change—with such "lengthening" of the time interval being permitted for a small number of additional, consecutive time intervals so that, if the patient goes to sleep, his or her medication is maintained at a reasonable level without radical adjustment in a downward direction.

Returning to the original example (i.e., to the system 100 input settings 102 as specified in the list that is presented above), if the patient operates the demand control twice per hour, this will represent a "normal" "demand" for analgesia, and will result in analgesia being delivered to the patient at the rate of 2 mg/hr. If the patient makes more than the "normal" 2 "demands" per hour for delivery of analgesia, the infusion rate will be adjusted so as to increase it. Applying the preset "rate adjustment factor" of 1 mg/hr, the increase will take place at 1 mg/hr so long as the number of "demands" made per hour continues to exceed the "normal" or "target" request rate of 2 per hour; however, the infusion rate per hour will not be increased beyond the preset maximum of 5 mg/hr. Likewise, if less than the "target" number of 2 demands is made per hour, the delivery rate will diminish by the "rate adjustment factor" of 1 mg/hr; however, the infusion rate per hour will not be diminished beyond the preset minimum of 0.1 mg/hr.

If, after loading the input information and starting the operation of the system 100, the patient is quite comfortable during the first hour (whereby he or she makes no demands for analgesia), the resulting lack of patient demand will cause the delivery rate of analgesia to be diminished by 1 mg/hr, whereby the "current rate" of delivery of analgesia will remain at the resulting 1 mg/hr rate for the second hour. However, if, during the second hour the patient emerges more fully from the anesthetic and initiates four demands for analgesia, the fact that the four demands exceeds the "target" rate will cause the infusion rate of analgesia to be increased by the rate adjustment factor of 1 mg/hr to a new "current rate" of 2 mg/hr.—and, if the demands are made at times that are spaced apart by more than the "lockout time," each of the demands will result in an incremental dose of 1 mg of analgesia being added as a supplement to the analgesia that is being delivered to the patient in accordance with the then-effective "current rate."

There are many additional factors that can be taken into account in the "instructions" or "pre-settings" or "programming" that is given to the system 100 so that the resulting delivery of analgesia to a patient will take place in an optimal manner. For example, the physician-prescribed input 102 to the system 100 and the patient demand input 120 to the system 100 can be supplemented as by providing a respiration rate sensor (not shown), the input from which is utilized by the system 100 to cause a cut back in infusion of analgesia if the respiration rate diminishes below a rate that is deemed to be acceptable. Likewise, other types of sensors (or devices other than sensors) can be utilized to determine characteristics of patient activity, pulse rate, time of day, and/or other factors that may give rise to needs for adjustments to be made in the manner in which the system 100 functions to deliver analgesia to a patient.

If desired, the system 100 can store data regarding drug delivery to a patient (and/or patient demand data) as a function of time-of-day so that, if a patient is to be provided with continuous drug infusion extending for a period of several days, the delivery of the drug can be controlled, at least in part, as by making "anticipatory need" adjustments that take into account the likelihood that the patient will need a different infusion rate at 7 A.M. than he will at 11 P.M. (i.e., adjustment on time-of-day being factored into "anticipated need" for drug infusion). If a patient's "need" can be anticipated on a time-of-day basis without first storing data that is relevant to the "actual need" of a particular patient, automatic time-of-day adjustment instructions can be given to the system 100 from the outset, with stored data being periodically checked to determine whether the initial "anticipation of need" on which time-of-day adjustments are being made should be modified in accordance with the observed "actual need" of a particular patient.

There are many different ways in which patient "demand" can be received by the system 100. If the patient is not capable of moving to push a button, voice activated controls or sensors that detect selected other inputs, including patient condition sensors, can be utilized to influence or to modify the operation of the system 100.

As will be apparent from the foregoing, discussion and examples, taken together with the accompanying drawing and claims, the system of the present invention provides a highly versatile patient-responsive, patient-controlled system for delivering liquid medicine such as analgesia to patients, with patient demand (and, if desired, other sensed factors) functioning in a plurality of ways to significantly influence the manner in which the system delivers drugs by infusion.

Significant advantages result from working with pre-set "target" figures for patient "demand" —and from utilizing the information that is gained by comparing "actual demand" to "targeted demand" to diminish or to increase or to maintain constant the delivery of medicine to patients. The system of the present invention utilizes pre-set target demand level to provide a patient responsive delivery system that is particularly well suited for use in infusing analgesia, and that functions automatically to curtail and minimize analgesia delivery in the absence of continued regular demand, whereby the rate of drug delivery to a particular patient will be held in close compliance with the actual needs of the patient, but within physician-prescribed limits.

Although the invention has been described in its preferred form with a certain degree of particularity, it is understood that the present disclosure of the preferred form is only by way of example, and that numerous changes in the details of carrying out the preferred practice of the claimed methods may be resorted to without departing from the spirit and scope of the invention as hereinafter claimed It is intended that the patent shall cover by suitable expression in the appended claims, whatever features of patentable novelty exist in the invention disclosed.

What is claimed is:

1. A method of administering liquid medicine such as analgesia to a patient as by infusion, comprising the steps of:

a) providing dispensing means having a reservoir for liquid medicine such as analgesia, a tube for delivering the liquid medicine to a patient as by infusion, and pre-settable dispensing means for controllably dispensing a flow of the liquid medicine from the reservoir into the tube, with the pre-settable dispensing means including control means for being operated to input control commands to the pre-settable dispensing means so as to regulate the dispensing of the liquid medicine from the reservoir into the tube, with the control means further including a patient demand control that is operable by a patient who is to be infused with the liquid medicine to register a need felt by the patient for the flow of medicine to continue to be dispensed, and with the control means also being operable to record the operations of the demand control by the patient so that decisions concerning the flow of dispensed liquid medicine can be made based, at least in part, on the record of felt need that has been registered by the patient as by operating the demand control;

b) dispensing liquid medicine from the reservoir through the tube for infusion delivery to the patient at an initial rate of flow, with the initial rate of flow residing within a predetermined range of acceptable flow rates that is bounded by an upper limit beyond which the dispensed flow rate is not to be permitted to rise, and by a lower limit beyond which the dispensed flow rate is not to be permitted to fall;

c) determining a predetermined target number of operations of the demand control per unit of measured time that is to be utilized to maintain an existing rate of flow of liquid medicine dispensed through the tube, and maintaining the then existing rate of flow of liquid medicine being delivered as by infusion to the patient so long as the actual number of operations of the demand control per unit of measured time equals the predetermined target number;

d) determining a first increment in rate of flow of dispensed medicine by which the existing flow rate of dispensed liquid medicine is to be increased in the event that the actual number of operations of the demand control per unit of measured time exceeds the target number by a first predetermined value, and, increasing the rate of flow of dispensed medicine by said first increment of flow rate in response to determining that the actual number of operations of the demand control per unit of measured time exceeds the target number by at least said first predetermined value;

e) determining a second increment in rate of flow of dispensed medicine by which the existing flow rate of dispensed liquid medicine is to be decreased in the event that the actual number of operations of the demand control per unit of measured time falls short of the target number by a second predetermined value, and, decreasing the rate of flow of dispensed medicine by said second increment of flow rate in response to determining that the actual number of operations of the demand control per unit of measured time falls short of the target number by at least said second predetermined value; and, f) continuing to dispense liquid medicine to the patient for infusion as by periodically adjusting the existing flow rate of dispensed medicine if variances between the actual number of operations of the demand control per unit of measured time exceeds or falls short of the target number by said first and second values, respectively, but with increases and decreases in said flow rate of dispensed medicine being curtailed as may be necessary to maintain the existing flow rate at all times within a predetermined range of safe values for flow rates to be used in dispensing medicine to the patient;

g) whereby, if the actual number of operations of the demand control per unit of measured time falls off due to sedation or diminished need of the patient, the flow rate at which medicine is dispensed to the patient by infusion likewise will diminish to insure safety and to conform the flow rate of medicine delivery to the minimal actual need of the client, but is maintained within said range of safe values for flow rates.

2. The method of claim 1 wherein said first predetermined value equals the number "one," whereby, if the actual number of operations of the demand control per unit of measured time exceeds the target number by even so much as the number "one," the rate of flow of dispensed medicine will be increased by said first increment of flow rate.

3. The method of claim 1 wherein said second predetermined value equals the number "one," whereby, if the actual number of operations of the demand control per unit of measured time falls short of the target number by even so much as the number "one," the rate of flow of dispensed medicine will be decreased by said second increment of flow rate.

4. The method of claim 1 wherein said first predetermined value equals a number greater than the number "one," whereby, if the actual number of operations of the demand control per unit of measured time exceeds the target number by said first predetermined value, the step of dispensing liquid medicine will not be increased until after the demand control has been operated a sufficient number of times to exceed the target number by said first predetermined value, thus the "responsiveness" to increased operations of the demand control as regards increasing the rate of flow of dispensed medicine will be determined and characterized by the selection of said first predetermined value.

5. The method of claim 1 wherein said second predetermined value equals a number greater than the number "one," whereby, if the actual number of operations of the demand control per unit of measured time falls short of the target number by said second predetermined value, the step of dispensing liquid medicine will not be decreased until after the demand control has fallen off to a sufficiently low number of operations per unit of measured time to fall short of the target number by said second predetermined value, thus the "responsiveness" to diminished operation of the demand control as regards decreasing the rate of flow of dispensed medicine will be determined and characterized by the selection of said second predetermined value.

6. The method of claim 1 wherein said first predetermined value and said second predetermined value are set to different numbers so that a) a "first level of responsiveness" to increased operations of the demand control as regards increasing the rate of flow of dispensed medicine will be determined and characterized by the selection of said first predetermined value, b) a "second level of responsiveness" to diminished operation of the demand control as regards decreasing the rate of flow of dispensed medicine will be determined and characterized by the selection of said second predetermined value, and c) said first level of responsiveness will differ from said second level of responsiveness.

7. The method of claim 6 wherein said first predetermined value is set to a number that is less than the number to which the second predetermined value is set, whereby the first level of responsiveness to increased operations of the demand control will cause an increase in the rate at which medicine is dispensed to a patient more readily than the second level of responsiveness to diminished operations of the demand control will cause a decrease in the rate at which medicine is dispensed to the patient.

8. The method of claim 1 for administering liquid medicine such as analgesia to a patient as by infusion, additionally comprising the steps of adding a predetermined dose of medicine to the quantity of liquid that is being dispensed for patient infusion, with said adding of a predetermined dose being done in response to operations of the demand control per unit of measured time when the number of operations of the demand control unit per unit of measured time exceeds said target number by a third predetermined value, but only if a predetermined lock-out interval of time has passed since the most recent earlier added predetermined dose was added to the quantity of liquid medicine that was dispensed, and only if the dispensing of an added dose will not take the amount of dispensed medicine above a safe predetermined limit for a given interval of time.

9. The method of claim 8 wherein the third predetermined value equals the number "one," whereby, if the actual number of operations of the demand control per unit of measured time exceeds the target number by even so much as the number "one," the rate of flow of dispensed medicine will be increased as by adding thereto said added predetermined dose, but only if a predetermined lock-out interval of time has passed since the most recent earlier added predetermined dose was added to the quantity of liquid medicine that was dispensed, and only if the dispensing of an added dose will not take the amount of dispensed medicine above a safe predetermined limit for a given interval of time.

10. The method of claim 8 wherein the third predetermined value equals a number greater than the number "one," and responsivity as by dispensing added predetermined doses of medicine in response to increased operations of the demand control per unit time in excess of the target number is determined, at least in part, by the number to which the third predetermined value is preset, with such responsivity effectively being diminished as by increasing the magnitude of the third predetermined value.

11. A method of administering liquid medicine such as analgesia to a patient through a tube, comprising the steps of:

a) dispensing liquid medicine at an initial rate of flow through a tube to a patient, with the rate of flow being held substantially constant for at least a predetermined interval of time, and with the rate of flow being selected to reside within a range of flow rates that is bounded at its upper and lower ends by maximum and minimum rates of flow that are predetermined as defining safe limits for said patient;

b) monitoring signals from an input device that is provided to the patient to enable the patient to periodically enter discrete requests for medicine;

c) adjusting the rate of flow of liquid medicine that is being dispensed through the tube, with the adjustment being made on a step-by-step basis in response to whether the number of monitored signals from the input device is less than, equal to, or greater than a predetermined target value during a measured unit of time, with the rate of flow being incrementally diminished at predetermined increments of flow rate so long as each successive number of monitored signals during each successive unit of time continues to remain lower than said target value, with the rate of flow being incrementally increased at predetermined increments of flow rate so long as each successive number of monitored signals during each successive unit of time continues to remain higher than said target value, but with no adjustment of flow rate being made so long as each successive number of monitored signals during each successive unit of time continues to equal said target value; and, d) maintaining a continuous flow rate of medicine being dispensed to the patient through the tube in accordance with steps a), b) and c) above, but assuring that the rate of flow does not exceed said maximum rate of flow, or fall below said minimum rate of flow, with a portion of said step of maintaining a continuous flow including the step of curtailing any adjustments that are implemented as the result of step c) to assure that the flow rate is maintained within said predetermined range of flow rates that are safe for said patient.

12. The method of claim 11 for dispensing liquid medicine to a patient through a tube, additionally comprising the step of adding a predetermined dose of medicine to the quantity of liquid that is being dispensed through the tube to the patient, with said adding of a predetermined dose being effected in response to monitored signals from the input device that exceed a predetermined value that is at least as large in magnitude as said target value, but only if a predetermined lock-out interval of time has passed since the most recent earlier added predetermined dose was added to the quantity of liquid medicine that is being dispensed to the patient, and only if the dispensing of the predetermined dose will not exceed said maximum rate of flow that defines the upper boundary said predetermined range of flow rates.

13. In a method of administering liquid analgesia to a patient as by intravenous infusion wherein a dispensing means is provided that is of the type having a reservoir for liquid analgesia, a tube for delivering the liquid analgesia to a patient as by intravenous infusion, and pre-settable control means for controllably dispensing a flow of the liquid analgesia from the reservoir into the tube, with the pre-settable control means being operable to receive, store and execute at instructed times an inputted series of commands so as to regulate the dispensing of the liquid analgesia from the reservoir into the tube, with the control means further including a patient demand control that is operable by a patient who is to be infused with the liquid analgesia to register a need felt by the patient for the flow of analgesia to continue to be dispensed, and with the control means also being operable to record the operations of the demand control by the patient so that decisions concerning the flow of dispensed liquid analgesia can be made based, at least in part, on the felt need that has been registered by the patient, wherein the improvement comprises the step of operating the dispensing means to carry out the following steps, comprising:

a) dispensing liquid analgesia from the reservoir of the dispensing means through the tube of the dispensing means for intravenous infusion delivery to the patient at an initial rate of flow, with the initial rate of flow residing within a predetermined range of acceptable flow rates that is bounded by an upper limit beyond which the dispensed flow rate is not to be permitted to rise, and a lower limit beyond which the dispensed flow rate is not to be permitted to fall;

b) determining a predetermined target number of operations of the demand control per unit of measured time that is to be utilized by the dispensing means to maintain an existing rate of flow of liquid analgesia dispensed through the tube, and maintaining the then existing rate of flow of liquid analgesia that is being delivered as by intravenous infusion to the patient so long as the actual number of operations of the demand control per unit of measured time equals the predetermined target number;

c) determining a first increment in rate of flow of dispensed analgesia by which the existing flow rate of dispensed liquid analgesia is to be increased in the event that the actual number of operations of the demand control per unit of measured time exceeds the target number by a first predetermined value, and, increasing the rate of flow of dispensed analgesia by said first increment of flow rate in response to determining that the actual number of operations of the demand control per unit of measured time exceeds the target number by at least said first predetermined value;

d) determining a second increment in rate of flow of dispensed analgesia by which the existing flow rate of dispensed liquid analgesia is to be decreased in the event that the actual number of operations of the demand control per unit of measured time falls short of the target number by a second predetermined value, and, decreasing the rate of flow of dispensed analgesia by said second increment of flow rate in response to determining that the actual number of operations of the demand control per unit of measured time falls short of the target number by at least said second predetermined value; and, e) continuing to dispense liquid analgesia to the patient for infusion as by periodically adjusting the existing flow rate of dispensed analgesia if variances between the actual number of operations of the demand control per unit of measured time exceeds or falls short of the target number by said first and second values, respectively, but with increases and decreases in said flow rate of dispensed analgesia being curtailed as may be necessary to maintain the existing flow rate at all times within a predetermined range of safe values for flow rates to be used in dispensing analgesia to the patient;

f) whereby, if the actual number of operations of the demand control per unit of measured time falls off due to sedation or diminished need of the patient, the flow rate at which analgesia is dispensed to the patient by infusion likewise will diminish to insure safety and to conform the flow rate of analgesia delivery to the minimal actual need of the client, but is maintained within said range of safe values for flow rates.

14. The method of claim 13 wherein said first predetermined value equals the number "one," whereby, if the actual number of operations of the demand control per unit of measured time exceeds the target number by even so much as the number "one," the rate of flow of dispensed medicine will be increased by said first increment of flow rate.

15. The method of claim 13 wherein said second predetermined value equals the number "one," whereby, if the actual number of operations of the demand control per unit of measured time falls short of the target number by even so much as the number "one," the rate of flow of dispensed medicine will be decreased by said second increment of flow rate.

16. The method of claim 13 wherein said first predetermined value equals a number greater than the number "one," whereby, if the actual number of operations of the demand control per unit of measured time exceeds the target number by said first predetermined value, the step of dispensing liquid medicine will not be increased until after the demand control has been operated a sufficient number of times to exceed the target number by said first predetermined value, thus the "responsiveness" to increased operations of the demand control as regards increasing the rate of flow of dispensed medicine will be determined and characterized by the selection of said first predetermined value.

17. The method of claim 13 wherein said second predetermined value equals a number greater than the number "one," whereby, if the actual number of operations of the demand control per unit of measured time falls short of the target number by said second predetermined value, the step of dispensing liquid medicine will not be decreased until after the demand control has fallen off to a sufficiently low number of operations per unit of measured time to fall short of the target number by said second predetermined value, thus the "responsiveness" to diminished operation of the demand control as regards decreasing the rate of flow of dispensed medicine will be determined and characterized by the selection of said second predetermined value.

18. The method of claim 13 wherein said first predetermined value and said second predetermined value are set to different numbers so that a) a "first level of responsiveness" to increased operations of the demand control as regards increasing the rate of flow of dispensed medicine will be determined and characterized by the selection of said first predetermined value, b) a "second level of responsiveness" to diminished operation of the demand control as regards decreasing the rate of flow of dispensed medicine will be determined and characterized by the selection of said second predetermined value, and c) said first level of responsiveness will differ from said second level of responsiveness.

19. The method of claim 18 wherein said first predetermined value is set to a number that is less than the number to which the second predetermined value is set, whereby the first level of responsiveness to increased operations of the demand control will cause an increase in the rate at which medicine is dispensed to a patient more readily than the second level of responsiveness to diminished operations of the demand control will cause a decrease in the rate at which medicine is dispensed to the patient.

20. The method of claim 13 for administering liquid analgesia to a patient as by intravenous infusion, additionally comprising the step of adding a predetermined dose of analgesia to the quantity of liquid analgesia that is being dispensed for patient infusion, with said adding of a predetermined dose being done in response to operations of the demand control per unit of measured time when the number of operations of the demand control unit per unit of measured time exceeds said target number by a third predetermined value, but only if a predetermined lock-out interval of time has passed since the most recent earlier added predetermined dose was added to the quantity of liquid analgesia that was dispensed, and only if the dispensing of an added dose will not take the amount of dispensed analgesia above a safe predetermined limit for a given interval of time.

21. The method of claim 20 wherein the third predetermined value equals the number "one," whereby, if the actual number of operations of the demand control per unit of measured time exceeds the target number by even so much as the number "one," the rate of flow of dispensed medicine will be increased as by adding thereto said added predetermined dose, but only if a predetermined lock-out interval of time has passed since the most recent earlier added predetermined dose was added to the quantity of liquid medicine that was dispensed, and only if the dispensing of an added dose will not take the amount of dispensed medicine above a safe predetermined limit for a given interval of time.

22. The method of claim 20 wherein the third predetermined value equals a number greater than the number "one," and responsivity as by dispensing added predetermined doses of medicine in response to increased operations of the demand control per unit time in excess of the target number is determined, at least in part, by the number to which the third predetermined value is preset, with such responsivity effectively being diminished as by increasing the magnitude of the third predetermined value.

23. A method for dispensing liquid medicine through a tube to a patient, a) wherein the medicine is of a type such as analgesia that is given to the patient for "relief" of an affliction, b) wherein the adequacy of the "relief" that is provided to the patient tends to increase as, within a safe range of dosages of medicine, the rate at which medicine is dispensed to the patient increases, and tends to decrease as the rate at which medicine is dispensed decreases, c) wherein the patient unto whom the "medicine is dispensed is provides "signals" as to the adequacy of the relief that he experiences as the result of the rate at which medicine is dispensed to the patient, and d) wherein the method of dispensing medicine comprises the steps of:
  a) providing the patient with a patient operable signaling device that the patient is to operate during each of a series of consecutive intervals of time that are of equal length, wherein the signals that are provided by the patient as the result of the operation of the signaling device during each of the intervals are counted an are interpreted such that:
   i) if the counted number of signals during a particular time interval is equal to a "target" number, the rate at which medicine is being dispensed to the patient is deemed to be adequate;
   ii) if the counted number of signals during a particular time interval is greater than said "target"

number, the rate at which medicine is being dispensed to the patient is deemed to be inadequate; and, iii) if the counted number of signals during a particular time interval is less than said "target" number, the rate at which medicine is being dispensed to the patient is deemed to be excessive;

b) determining a safe range of rates for dispensing medicine to the patient that is deemed to be desirable for use with the particular patient, and, initiating a continuous-flow dispensing rate of medicine to the patient that is well within said safe range of rates;

c) utilizing the counted signal information that is provided by the patient's operation of the signalling device to determine not only how the continuous-flow dispensing of the medicine to the patient is to be adjusted within said safe range of rates, but also to determine when a supplemental interval dose of medicine of a predetermined magnitude is to be dispensed through the tube to the patient, wherein:

i) if the counted number of signals within a particular time interval is equal to said "target" number, A) the rate at which medicine is being dispensed to the patient is maintained, and B) the rate at which medicine is being dispensed to the patient is not supplemented by any supplemental interval doses—whereby, the dispensing of medicine through the tube to the patient is held at a rate that the patient has signalled is adequate;

ii) if the counted number of signals within a particular time interval is greater by a first predetermined value than said "target" number, A) the rate at which medicine is being dispensed to the patient is increased as by a predetermined incremental amount except that, if the upper end value of the safe range of rates is reached, the upper end value is not exceeded, and B) the rate at which medicine is being dispensed to the patient briefly is supplemented as by dispensing a supplemental interval dose of a predetermined quantity of medicine through the tube to the patient—whereby the dispensing of medicine through the tube to the patient is increased to a rate of flow that is more in conformance with what the patient has signalled that he deems is needed; and, iii) if the counted number of signals within a particular time interval is less by a second predetermined value than said "target" number, A) the rate at which medicine is being dispensed to the patient is decreased as by a predetermined incremental amount except that, if the lower end value of the safe range of rates is reached, the lower end value is not exceeded, and B) the rate at which medicine is being dispensed to the patient briefly is not supplemented as by dispensing a supplemental interval dose of a predetermined quantity of medicine through the tube to the patient—whereby the dispensing of medicine through the tube to the patient is decreased to a rate of flow that is more in conformance with what the patient has signalled that he deems is needed.

24. The method of claim 23 wherein the first predetermined value and the second predetermined value are set so as to suitably govern the degree of responsiveness to which changes are made in the rate at which medicine is dispensed to the patient as variations in counted signals per interval of time from the target number are encountered during the dispensing of medicine to the patient.

25. The method of claim 24 wherein the first and second predetermined values are set to provide different degrees of responsiveness to govern increases as opposed to decreases in the rates at which medicine is dispensed to the patient.

* * * * *